(12) United States Patent
Poznansky et al.

(10) Patent No.: US 7,695,712 B2
(45) Date of Patent: Apr. 13, 2010

(54) RECOVERY OF TISSUE FUNCTION FOLLOWING ADMINISTRATION OF B CELLS TO INJURED TISSUE

(75) Inventors: Mark C. Poznansky, Charlestown, MA (US); Traci T. Goodchild, Dunwoody, GA (US); Mark T. Ungs, Minnetonka, MN (US); Nicholas A. F. Chronos, Atlanta, GA (US); Nadine Weich, Brookline, MA (US)

(73) Assignee: ACTX, Inc., Atlanta, GA (US)

( * ) Notice: Subject to any disclaimer, the term of this patent is extended or adjusted under 35 U.S.C. 154(b) by 166 days.

(21) Appl. No.: 11/406,508

(22) Filed: Apr. 18, 2006

(65) Prior Publication Data

US 2006/0263339 A1    Nov. 23, 2006

Related U.S. Application Data

(60) Provisional application No. 60/672,416, filed on Apr. 18, 2005.

(51) Int. Cl.
*C12N 5/0781* (2006.01)
*A01N 65/00* (2006.01)
(52) U.S. Cl. .................... 424/93.7; 435/372; 435/372.2
(58) Field of Classification Search ........................ None
See application file for complete search history.

(56) References Cited

U.S. PATENT DOCUMENTS 6,051,230 A * 4/2000 Thorpe et al. ............. 424/178.1
6,465,251 B1 * 10/2002 Schultze et al. ............. 435/377

FOREIGN PATENT DOCUMENTS

WO    WO 2004/044584    5/2004

OTHER PUBLICATIONS

Boctor et al. "Cryoglobulinemia and cutaceous vasculitis". Transfusion (Malden), Feb. 2004, vol. 44, No. 2, p. 145.*
Burney-Taney et al. The Journal of Immunology. 2003. 171: 3210-3215.*
American Heart Association. *Heart and Stroke Update*. Dallas, TX: American Heart Association; 2003.
Barbul, A., "Role of T-cell-dependent immune system in wound healing." *Prog. Clin. Biol. Res.*, 1988, 266:161-175.
Funderud, S., et al., "Functional properties of CD19+B lymphocytes positively selected from buffy coats by immunomagnetic separation." *Eur. J. Immunol.*, 1990, 20(1):201-206.
Gulbins, H., et al., "Cell transplantation—A potential therapy for cardiac repair in the future?" *Heart Surg. Forum* 2002; vol. 5(4):E28-34.
Kloner, R.A., et al., "Consequences of Brief Ischemia: Stunning, preconditioning, and their clinical implications: part 1." Circ. 2001; 104:2981-2989.
Miltenyi, Biotec sells kits with protocols to isolate B cells and plasma cells from tissue.

Monfalcone, et al., "Increase leukocyte diversity and responsiveness to B-cell and T-cell mitogens in cell suspensions prepared by enzymatically dissociating murine lymph nodes." *J. Leukoc. Biol.*, 1986, 39(6):617-28.
Niimi, M., et al., "Intrathymic administration of B cells induces prolonged survival of fully allogenic cardiac grafts without prolonged deletion of donor-specific thymocytes." *Transplant Immunology*, 1998; 6:177-181.
Witte, M.B., et al., "General principals of wound healing." *Surg. Clin. North Am.*, 1997, 77:509-528.
Zhang, M., et al., "Identification of a specific self-reactive IgM antibody that initiates ischemia/reperfusion injury." *Proc. Natl. Acad. Sci. USA*, 2004, 101:3886-3891.
Akashi et al., B Lymphopoiesis in the Thymus, Journal of Immunology, 2000, 164(10):5221-5226.
Bauer et al., Isolation of Human B-Cell Subpopulations for Pharmacological Studies, Biotechnology Progress, 1991, 7:391-396.
Burne-Taney et al., Effects of Combined T- and B-Cell Deficiency on Murine Ischemia Reperfusion Injury, American Journal of Transplantation, 2005, 5:1186-1193.
Chang et al., Early Fetal Liver Readily Repopulates B Lymphopoiesis in Adult Bone Marrow, Stem Cells, 2005, 23(2):230-239.
European Supplementary Search Report for European Patent Application No. 06750473, mailed Oct. 29, 2008.
Ikeda et al., Ischemic Acute Tubular Necrosis Models and Drug Discovery: A Focus on Cellular Inflammation, Drug Discovery Today, 2006, 11(7/8):364-370.
Kodituwakku et al., Isolation of Antigen-Specific B Cells, Immunology and Cell Biology, 2003, 81:163-170.
American Heart Association. *Heart and Stroke Update*. Dallas, TX: American Heart Association; 2003.
Barbul, A., "Role of T-cell-dependent immune system in wound healing." *Prog. Clin. Biol. Res.*, 1988 266:161-175.
Funderud, S., et al., "Functional properties of CD19+B lymphocytes positively selected from buffy coats by immunomagnetic separation." *Eur. J. Immunol.*, 1990, 20(1):201-206.
Gulbins, H., et al., "Cell transplantation—A potential therapy for cardiac repair in the future?" *Heart Surg. Forum* 2002; vol. 5(4):E28-34.
Kloner, R.A., et al., "Consequences of Brief Ischemia: Stunning, preconditioning, and their clinical implications: part 1." Circ. 2001; 104:2981-2989.
Monfalcone, et al., "Increase leukocyte diversity and responsiveness to B-cell and T-cell mitogens in cell suspensions prepared by enzymatically dissociating murine lymph nodes." *J. Leukoc. Biol.*, 1986, 39(6):617-28.

(Continued)

*Primary Examiner*—Vera Afremova
(74) *Attorney, Agent, or Firm*—Kilpatrick Stockton LLP (57) ABSTRACT

The present invention relates generally to systems and methods of enhancing recovery of function of injured tissue through administration of a composition comprising a relatively pure populations of B lymphocyte cells in a pharmaceutically acceptable carrier to the injured tissue. Kits are provided to aid in purification of B cells from heterogeneous mixtures of cells and administration of B cells to injured tissue.

11 Claims, 5 Drawing Sheets

OTHER PUBLICATIONS

Niimi, M., et al., "Intrathymic administration of B cells induces prolonged survival of fully allogenic cardiac grafts without prolonged deletion of donor-specific thymocytes." *Transplant Immunology*, 1998; 6:177-181.

Witte, M.B., et al., "General principals of wound healing." *Surg. Clin. North Am.*, 1997, 77:509-528.

Zhang, M., et al., "Identification of a specific self-reactive IgM antibody that initiates ischemia/reperfusion injury." *Proc. Natl. Acad. Sci. USA*, 2004, 101:3886-3891.

* cited by examiner

RECOVERY OF TISSUE FUNCTION FOLLOWING ADMINISTRATION OF B CELLS TO INJURED TISSUE

PRIOR RELATED APPLICATIONS

The present applications claims the benefit of priority to U.S. provisional patent application Ser. No. 60/672,416 filed Apr. 18, 2005, which is incorporated herein by reference in its entirety.

FIELD OF THE INVENTION

The present invention relates generally to methods of enhancing recovery of tissue function following injury through administration of relatively pure populations of B lymphocytes to injured tissue.

BACKGROUND

Loss of tissue function, whether by disease or accident, remains a major health problem. Heart and brain injuries, for example, are two of the leading causes of death and disability throughout the world. In the United States, cardiac disease accounts for 40% of all deaths and is the leading cause of congestive heart failure (American Heart Association. *Heart and Stroke Update*. Dallas, Tex.: American Heart Association; 2003). Cardiac disease that leads to acute myocardial infarction or chronic myocardial ischemia can also cause significant degradation in cardiac function. If the ischemic episode is limited in severity or duration, then cardiomyocytes survive and are protected from further ischemic insult through several preconditioning mechanisms. However, with acute and prolonged severe periods of ischemia, cardiomyocyte death occurs (Kloner R A, et al., Consequences of brief ischemia: stunning, preconditioning, and their clinical implications: part 1. Circ. 2001; 104:2981-2989). Under normal conditions, adult human cardiomyocytes lack the capability to regenerate, and over time, damaged myocardial cells are replaced by connective scar tissue along with a compensatory hypertrophy of the remaining viable cardiomyocytes (Gulbins H, et al., Cell transplantation-A potential therapy for cardiac repair in the future? *Heart Surg Forum* 2002; Vol 5(4):E28-34). This replacement of infarct by scar tissue leads to a loss of functional myocardium within the ischemic area, a progressive remodeling of the non-ischemic area, or border zone, and an overall reduction in cardiac performance.

Stroke is the third leading cause of death in the United States and the number one cause of adult disability. Ischemic stroke caused by blood flow interruption to the brain due to blockage of an artery by a blood clot accounts for about 70-80 percent of all strokes. A loss of blood flow to the brain deprives an area of brain cells of oxygen and nutrients which results in cell death. Body functions controlled by the area of the brain that has been damaged are lost. These functions include speech, movement and memory.

Repair of injured tissue is a complex process that begins at the moment of injury and can continue for months to years. This process can be broken down into three major phases; inflammatory, proliferative and remodeling. (Witte M B, et al. General principals of wound healing. *Surg Clin North Am* 1997, 77:509-528).

The inflammatory phase is immediate and can last for 5 to 7 days. During this phase, if there is tissue damage and/or cellular disruption as with trauma, vasoconstriction occurs and a clot forms which serves as a temporary protective shield for the exposed or damaged tissues. The clot provides cytokines and growth factors released by activated platelets that initiate the wound closure process and chemotactic signals to recruit circulating inflammatory cells to the wound site. Vasodilation follows and phagocytosis is initiated.

The proliferative phase is next and can last up to three weeks. During this phase granulation commences and involves the formation of a bed of collagen by fibroblasts which results in the filling of the defect. New capillaries are formed in a process called granulation tissue formation, which is followed by contraction in which the wound edges come together to reduce the lesion. The last stage of the proliferative phase is re-epithelialization. In skin wound healing, keratinocytes move in all directions from a point of origin across a provisional matrix to cover the wound.

The final phase of tissue repair is the remodeling phase. It can last up to two years and includes the production of new collagen which continues to increase the tensile strength of the wound.

The immune system has been recognized as an important regulator of tissue repair. It is composed of two parts, humoral and cellular defenses. The humoral arm includes antibodies and complement and little is known about the role that this arm plays in the process of tissue repair. On the other hand, much is known of the cellular arm which includes neutrophils, macrophages and T lymphocytes. These cell populations migrate into the wound in an ordered timeframe and contribute to the repair process through the secretion of signaling molecules in the forms of cytokines, lymphokines and growth factors. (Witte M B, et al., General principals of wound healing. *Surg Clin North Am* 1997, 77:509-528). Neutrophils are the first cells to appear at the wound site and are responsible for phagocytosis and debridement. Macrophages are the next cells to migrate into the wound. They complete the inflammatory and debridement processes and deliver critical tissue repair cytokines and growth factors. T lymphocytes are the last cells to migrate into the lesion and appear during the proliferative phase and their role includes the downregulation of the inflammatory response and growth state as this phase of the process concludes (Barbul A., Role of T-cell-dependent immune system in wound healing. *Prog Clin Biol Res* 1988, 266:161-175). Not all cells in the immune system are believed to participate in the tissue repair process. The role of B cells (B lymphocytes) in tissue repair, for example, is unclear and is presumed by those knowledgeable in the field to be inconsequential since helper T2 cell cytokines and B lymphocyte activating factors have not been detected at the wound site. What little amount of evidence exists on the role of B cells in tissue repair suggests B cells have a pathogenic role (Zhang M, et al., Identification of a specific self-reactive IgM antibody that initiates ischemia/reperfusion injury. *Proc Natl Acad Sci USA* 2004, 101:3886-3891).

Instead, B cells are best known for the role they play in the production of antibodies. They are generated from hematopoietic stem cells (HSCs) throughout life, first in the fetal liver and then in the adult bone marrow. Cytoplasmic cascades are initiated in response to tissue microenvironment signals that result in altered expression of proteins required for B cell maturation. The mature bone marrow B cell expresses IgD on its surface membrane which protects it from self antigen induced death. This mature cell moves into the periphery where it can be activated by antigen to become either an antibody-secreting plasma cell or a memory B cell.

While treatment options available to patients who have lost tissue function have increased recently, these options remain limited in their effectiveness. New therapies that can limit the amount of cell death and restore loss of body function are greatly needed. An appealing concept for the treatment of tissue injury is cell-based therapy. Evidence of cells engrafting into the damaged tissue coupled with an improvement of function supports this approach. However, the most appropriate cell type has yet to be defined. While many groups are eager to begin treating patients with various cells, researchers are just now beginning to understand some of the mechanisms of how these cells repair injured tissue. What is needed is an identification of which cell, or combination of cells, is most appropriate for the repair of damaged tissue.

While many different cell therapy methods are being tried, the common goal in cell therapy is the introduction into injured tissue of a cell that is either functionally related to the targeted tissue, such as with delivery of skeletal myoblasts into damaged myocardium, or primordial cells (stem or progenitor cells) that are hoped will regenerate new tissue and structures thereby returning function to the injured organ. The bone marrow is a well understood source of stem cells for a variety of tissue but primarily for the blood system. Early attention was given to the bone marrow as a source of potentially therapeutic cells after several studies demonstrated that animals with labeled bone marrow cells that were subjected to a tissue injury such as a myocardial infarction were found to have some of these labeled bone marrow cells integrated into the healing tissue. However, while integration of bone marrow derived cells into healed tissue was demonstrated, many questions remain unanswered including what cell type from the bone marrow integrated into the tissue and the extent to which these cells contributed to the functional recovery of the injured tissue. Nonetheless, there was sufficient potential of a therapeutic effect for research to proceed in this field including human experimentation. Experimentation into bone marrow derived cell therapy has utilized either the entire bone marrow, also known as unfractionated bone marrow, or the isolation of the endothelial progenitor, hematopoietic (CD34+, AC133+) and nonhematopoietic (CDstrol+) stem cells contained within it. While the experimental use of unfractionated bone marrow, bone marrow derived progenitor, and stem cells continues, early results from their use have been disappointing due to only modest improvement or negative outcomes, questioning the relevance of the earlier animal experimentation and the therapeutic value of bone marrow derived cells.

SUMMARY OF THE INVENTION

The present invention addresses the problems described above by providing compositions and methods for improving tissue function following injury. Our invention demonstrates for the first time that cells of the B cell lineage including pre-pro-B cells, pro-B cells, pre-B cells, immature B cells, and some mature B cells, when transplanted into damaged tissue have the ability to enhance recovery following injury.

It is to be understood that the methods of the present invention may be applied to any animal. It is further to be understood that the term "animal" includes a "human" in the present application.

B cell therapy has the potential to promote repair in many different types of tissues including but not limited to heart, brain, kidney, muscle and lung. It is a surprising finding of the present invention that administration of B lymphocytes to ischemic cardiac tissue improves recovery of cardiac function. B lymphocytes are preferred cells of the present invention for administration to the ischemic cardiac tissue. Injection of these cells improves cardiac function. The present invention reveals that administration of an effective amount of B lymphocytes or modified versions thereof improves the function of injured tissue. In a preferred embodiment, the present invention reveals that administration of an effective amount of B lymphocytes or modified versions thereof improves cardiac function. Modified B cells include B cells that are subjected to hypoxia or chemical changes, are genetically modified, or are otherwise altered by exposure to varying chemical or physical conditions. These conditions may include but are not limited to temperature, pressure, osmotic conditions, pH, and varying concentrations of molecular compounds, electrolytes, and proteins such as B cell activating factor, and similar agents.

A preferred type of cell which is administered to injured tissue is the beta (B) lymphocyte and its precursors, hereinafter called a B cell or B lymphocyte. Any type of B cell may be used. B cells can be characterized by the presence of specific surface proteins, as known to one of ordinary skill in the art. These include but are not limited to B220, CD19, CD43, CD45RA, CD5, Mac-1, IgM, IgD, IgG, CD62L, CD23, CD21, CD40 and B cell receptor (Ig$\alpha\beta$). In one embodiment the B cells are human B cells and are characterized by having one or more CD19, B220 or B cell receptor (Ig$\alpha\beta$) surface proteins. The present invention describes studies performed in rats using antibodies to the CD45RA antigen, which is a member of the CD45 antigen family that also includes the CD45, CD45RB, and CD45RO antigens.

The present invention reveals that B cells used for treating injured tissue should be relatively pure and should not contain appreciable numbers of stem cells. In the present application, relatively pure means at least 80% pure, 85% pure, 88% pure, or even higher degrees of purity such as at least 90% pure, preferably at least 95% pure, preferably at least 97% pure, or preferably at least 98% pure as determined by fluorescence activated cell scan (FACS) analysis. The B cell population in the bone marrow is heterogeneous, containing pre-pro-B cells, pro-B cells, pre-B cells, immature B cells, and some mature B cells. In some experiments reported in the present application, when the CD45RA antibody is used to isolate the B cells from the bone marrow of rats, all of these different types of B cells are obtained and used for administration into the animal. While not wanting to be bound by the following statement, it is believed that any type of B cell, or combinations thereof, may be used in the method of the present invention.

B cells may be administered directly into the injured tissue, into tissue surrounding the injury, topically, intracerebroventricularly, intramuscularly, intramyocardially, intrarenally, intrahepatically or systemically. In one embodiment, B cells may be administered into infarcted myocardium or into myocardium surrounding the infarcted tissue. Injection of cells into the ischemic cardiac tissue or through the cardiac vasculature enhances cardiac function following infarction. The methods of the present invention can be used for lessening the decline in cardiac function following an ischemic episode. Further, the methods of the present invention improve cardiac function following ischemia or following ischemic injury. This improvement in cardiac function provides a better quality of life or longevity for such individuals, enabling them to engage in physical activities that might be otherwise proscribed or contraindicated. By restoring cardiac function following ischemia, use of the method of the present invention decreases the chance of cardiac arrest following an episode of cardiac ischemia.

The present invention includes methods for increasing the concentration of B cells at a desired site, such as injured tissue, by administering a substance that binds to the B cell and also to a binding site in the vicinity of the injured tissue or to a binding site on a device located adjacent to the injured tissue. Such a substance may be a bifunctional antibody that may, for example bind to CD19 antigens on B cells and also to a binding site located in the vicinity of the injured tissue or to a binding site on a device located adjacent to the injured tissue. In this manner, the number of B cells in the vicinity of the injured tissue is increased. This method may be used whether the B cells are resident in the animal or the human, or are harvested, purified and administered to the animal or the human.

The present method may be used to treat other conditions related to poor perfusion or less than normal blood flow and oxygenation, including but not limited to the following: peripheral vascular disease, decreased tissue perfusion in diabetics for example in tissue located in the extremities, decreased cardiac perfusion in patients with atherosclerosis of one or more coronary arteries, decreased cardiac perfusion in patients undergoing bypass surgery or another cardiac procedure, renal disease including ischemic renal diseases, decreased cranial perfusion in patients with atherosclerosis of one or more carotid arteries or branches thereof, or with atherosclerosis of one or more vertebral arteries or other arteries in the cerebrovascular circulation, temporary ischemic episodes, stroke, occlusion of vessels due to trauma, a mass, or any other cause.

The present invention is not limited to treatment of ischemic tissue or cardiac tissue. B cells may be administered to any injured tissue. Trauma, disease, chemical or other environmental exposures are other proximate causes. Ischemia is one type of condition that produces injured tissue. Preferably, B cells are administered to tissue following any injury. Tissue injury may result from many different causes. For example, tissue injury may occur following ischemia, hemorrhage, organ transplant, trauma, surgery, inflammation, infection, burns, disease progression, aging or many other causes.

B cells may also be administered in conjunction with other forms of therapy. Substances which may be co-administered include but are not limited to the following: stem cell mobilizing agents (GM-CSF, SDF, GCSF, platelet-derived growth factor (PDGF)); growth factors VEGF, FGF, IGF-1; nitric oxide donors such as nitroglycerin; COX-2 inhibitors; diuretics, angiogenic factors (VEGF, angiostatin inhibitors); factors that enhance blood flow; anti-inflammatories; anti-hypertensives; HMG co-reductase inhibitors; statins; angiotensin converting enzyme (ACE) inhibitors; wound healing enhancers; NSAIDS; chemokine antagonists; thrombin; extracellular molecules; chemokines including but not limited to CXCL12, CXCL13, CCL19, CCL21, CCL25, CXCL9, and CXCL10; integrin ligands including but not limited to MADCAM1 (mucosal addressin cell-adhesion molecule 1) and VCAM1 (vascular cell-adhesion molecule 1); interleukin-4; and factors including any environmental cues that enhance the survival and effectiveness of the B lymphocytes or combinations thereof.

It is believed that the present method may be used to enhance perfusion of less than adequately perfused tissue and to enhance a cell's ability to withstand ischemic conditions, thereby preventing or substantially delaying the onset of damaging ischemic episodes. Such therapy is also beneficial in patients with sub-optimal perfusion of tissue such that the tissue performs better in situations of enhanced demand, for example, during exercise.

While not wanting to be bound by the following statement, it is believed that the administration of B cells to cardiac tissue may activate resident cardiac stem or progenitor cells in or near the infarcted cardiac tissue, enhance a cell's ability to withstand ischemic conditions, and inhibit the breakdown of collagen.

The present method may also be used for improving cardiac function in patients who are not candidates for bypass surgery.

The present invention also provides kits which may be used to prepare relatively pure populations of B cells that may be used subsequently for administration to ischemic tissue. Such kits include various antibodies known to one of ordinary skill in the art that are useful in selecting and separating desired cells from a heterogeneous population of cells. These antibodies generally comprise primary antibodies that recognize surface antigens, such as proteins, polypeptides and glycoproteins that are characteristic of specific cells and are known to one of ordinary skill in the art. These kits may include such antibodies that recognize these surface antigens. Directions for using a kit are enclosed with each kit.

These kits may include materials and apparatus used in harvesting B cells. For example, if the B cell is obtained from bone marrow, these kits may include an 11 gauge tapered needle device designed to penetrate into the interior of bone usually the posterior superior ilium but sometimes the sternum, iliac crest, tibia or femur. Once penetrated, a polycarbonate syringe is attached and a vacuum applied to obtain the marrow.

The kits include antibodies and materials that are specific for the cell type to be isolated, for example B cells, and may be further specialized for use in the heterogeneous cell mixture obtained from a specific tissue or organ. Materials may include apparatus or reagents useful in separation or preparation such as tubing conduits, separators, filtrators, and containers, incubation apparatus including tissue culture equipment and containers, and chemical or molecular reagents. That is, isolation of B cells from a cell preparation from bone marrow may require the use of an antibody or antibodies specific for the surface antigens on the bone marrow derived B cells. In addition, such a kit may include an antibody or antibodies specific for the surface antigens on the bone marrow derived cells to be separated from the desired bone marrow derived B cells. In this manner, a positive selection technique may be used optionally in combination with a negative selection technique. In order to facilitate negative selection, kits may be designed to include antibodies that are specific for all cell types except for the type to be isolated, for example B cells, in order to isolate the cell type through negative selection. The tools contained in these kits may be constructed of materials such as plastics, stainless steel, nitinol, rubber and other materials that bind, concentrate or exclude cells. The kits may also contain primary antibodies that are labeled so that the labeled cells may be separated by techniques know to one of ordinary skill, including but not limited to immunomagnetic separation. Such labels are commercially available. These kits may optionally contain secondary antibodies, which themselves may be labeled, and which may bind to the primary antibodies. Labels that may be attached to antibodies are known to one of ordinary skill in the art and include, but are not limited to, light emitting labels and magnetically responsive labels. Antibodies may be stored in containers in the kits which may be customized for protection from light, heat or other undesirable conditions. Antibodies may be stored in a lyophilized state or in a convenient buffer system optionally containing a preservative. Kits may also contain pharmaceutically acceptable buffers for use in handling samples during purification and elution steps, and for suspension of the isolated B cells for storage or for subsequent administration to the cell donor.

In one embodiment, kits may contain antibodies for positive selection, negative selection or both, in the form of affinity columns. Such columns may contain antibodies bound at their Fc region to a matrix within the columns. Heterogeneous cell preparations may be introduced into the affinity column.

These kits may also contain containers for mixing the antibodies with the cell preparations, means to transfer solutions such as pipetting means, graduated flasks, graduated centrifuge tubes, and the like. Further, the kits may include prepackaged closed systems to insure sterility.

These kits may also contain devices for the delivery of the B cells. A variety of devices may be included depending on the targeted delivery site. Intravascular and transcutaneous delivery could be achieved with standard syringes while delivery to the brain, heart and kidney may involve specialized transluminal devices that allow for the infusion or direct injection of cells into or around the targeted organ.

Accordingly, it is an object of the present invention to provide a method to enhance recovery of function in injured tissue through administration of B cells to the injured tissue, in the vicinity of the injured tissue or through other means leading to the injured tissue.

It is an object of the present invention to provide a method to enhance recovery of cardiac function in injured cardiac tissue through administration of B cells to the injured cardiac tissue or in the vicinity of the injured cardiac tissue.

It is another object of the present invention to provide an effective amount of relatively pure B cells for administration to the injured tissue or in the vicinity of the injured tissue.

Another object of the present invention is to provide kits useful for obtaining B cells and purifying B cells for subsequent administration to a human.

Another object of the present invention is to provide kits useful in separation of B cells from other cells in a heterogeneous cell population.

An advantage of the present invention is that injured tissue is improved following administration of B cells, resulting in enhanced function and quality of life, and decreased morbidity and mortality.

An advantage of the present invention is that cardiac function is improved following administration of B cells to ischemic cardiac tissue, resulting in enhanced cardiovascular function and quality of life, and decreased chance of cardiac arrest.

These and other objects, features and advantages of the present invention will become apparent after a review of the following detailed description of the disclosed embodiments and claims.

BRIEF DESCRIPTION OF THE FIGURES

FIG. 2: Primary screen monitoring cardiac contractility following injection of specific populations of bone marrow cells post ischemic injury. Bone marrow was harvested from donor Sprague-Dawley rat femurs and tibias and various cell populations isolated. Six recipient rats underwent ligation of the left anterior descending coronary artery and saline, $1 \times 10^6$ HSCs, $5 \times 10^5$ HSCs combined with $5 \times 10^5$ B cells, or $1 \times 10^6$ B cells alone were directly injected into the infarcted area. After 2 weeks, the surviving animals (5 to 6 rats) underwent follow-up echocardiography and hemodynamic measurements including cardiac contractility (dP/dT). Sham operated (no ligation) and ligation plus saline injection animals were included as controls. Note the degradation of the heart's contractility measured by +dP/dT as well as the heart's ability to relax measured by −dP/dT when HSCs combined with B cells are injected and the improvement of these parameters when B cells alone are injected.

FIG. 3: B cells reproducibly augment cardiac function following ischemic injury. Bone marrow was harvested from donor Sprague-Dawley rat femurs and tibias and B lineage and stem cell populations isolated. The recipient rats underwent ligation of the left anterior descending coronary artery and a total of 1 million freshly isolated cells (HSC and B cells) or overnight cultured cells (Cultured B cells and B cells co-cultured with non-hematopoietic stem cells (NHSCs)) were injected immediately after ligation into the infarcted area. After 2 weeks, the surviving animals underwent follow-up echocardiography and hemodynamic measurements. Percent of ventricular short-axis diametric shortening was monitored as a measure of cardiac function and analysis of variance (ANOVA) was performed to determine data significance. Sham operated (no ligation), ligation plus saline and HSC injection animals were included as controls.

DETAILED DESCRIPTION OF THE INVENTION

The present invention provides a new, effective and efficient method for treating injured tissue, through administration of an effective amount of B cells. Tissue injuries arise from numerous causes, including but not limited to, ischemia, diabetes and other chronic diseases, organ and tissue transplant, trauma, burns, stroke (both ischemic and hemorrhagic), infection, inflammation, surgery and other causes. The B cells to be administered are preferably autologous cells and are harvested from the donor using techniques known to one of ordinary skill in the art. Sources of such B cells are generally known and include, but are not limited to bone marrow, blood, spleen, lymph nodes, and allogeneic sources. B cells are then purified from the heterogeneous cell population in order to obtain a relatively pure population of B cells. Such purification techniques are described in the present application. Kits are provided to purify B cells from the heterogeneous cell populations.

The present invention provides for the use of B cells in the preparation of a medicament for administration to an animal or a human, wherein the medicament is useful in treating injured tissue. Such medicaments may include a pharmaceutically acceptable carrier. Such medicaments may optionally include another substance that facilitates restoration of function of the injured tissue or the function and/or survival of the relatively pure population of B cells administered to the animal or the human. It is to be understood that the methods of the present invention may be applied to any animal. It is to be understood that the term "animal" includes a "human" in the present application.

The B cells may be administered in conjunction with other therapies known to one of ordinary skill in the art for enhancing tissue repair or for enhancing the retention, efficacy, and survival of the B cells administered to the damaged tissue. The present invention provides kits useful in the separation and purification of B cells from heterogeneous cell mixtures.

While the present invention may be used to treat different types of damaged tissue, cardiac tissue is a preferred tissue to be treated with the present invention.

Preparation of B Cells

Any source of B cells may be used in the present invention. Such B cells may be derived from the bone marrow, spleen, lymph nodes, blood or other allogeneic tissues that are sources of B cells, as known to one of ordinary skill in the art. Preferred sources of B cells are bone marrow and blood. References for such methods include: Funderud S, et al., Functional properties of CD19+ B lymphocytes positively selected from buffy coats by immunomagnetic separation. Eur J Immunol 1990 20(1):201-6; Monfalcone et al., Increase leukocyte diversity and responsiveness to B-cell and T-cell mitogens in cell suspensions prepared by enzymatically dissociating murine lymph nodes. J Leukoc Biol 1986 39(6): 617-28; and, Miltenyi Biotec sells kits with protocols to isolate B cells and plasma cells from tissue.

Using sterile techniques known to one of ordinary skill in the art, in one embodiment, bone marrow is preferably obtained from the posterior superior ilium. The B cells obtained with the present method may be immediately used after isolation and relative purification, may be stored for subsequent use, or may be cultured for a period of time before use. The B cell population in the bone marrow contains pre-pro-B cells, pro-B cells, pre-B cells, immature B cells, and some mature B cells. In the present application, the term B cell encompasses pre-pro-B cells, pro-B cells, pre-B cells, immature B cells, and mature B cells. From blood or other tissues, B cells can be isolated using techniques known to one of ordinary skill in the art. The results of the present invention demonstrate that these B cells should be relatively free from stem or progenitor cells when administered to a recipient.

Method to Obtain B Cells or Progenitor B Cells from Heterogeneous Cell Populations Methods to obtain B cells or precursor B cells from heterogeneous cell populations are known to one of ordinary skill in the art. Many of these techniques employ primary antibodies that recognize molecules on the surface of the desired B cells or B cell precursors and use these antibodies to positively select these cells and separate them from unwanted cells. This technique is known as positive selection. Other techniques commonly employed by one of ordinary skill in the art use primary antibodies that recognize molecules on the surface of the cells to be separated from the desired B cells or B cell precursors. In this manner, molecules on these unwanted cells are bound to these antisera and these cells are removed from the heterogeneous cell population. This technique is known as negative selection. A combination of positive and negative selection techniques may be employed to obtain relatively pure populations of B cells or precursor B cells. In the present application, relatively pure means at least 80% pure, 85% pure, 88% pure, or higher degrees of purity such as at least 90% pure, at least 95% pure, at least 97% pure, or at least 98% pure.

Numerous techniques are available to one of ordinary skill to separate antibodies bound to cells. Antibodies may be linked to various molecules that provide a label or tag that facilitates separation. In one embodiment, primary antibodies may be linked to magnetic beads that permit separation in a magnetic field. In another embodiment, primary antibodies may be linked to fluorescent molecules that permit separation in a fluorescent activated cell sorter. Fluorescent and magnetic labels are commonly used on primary and/or secondary antibodies to achieve separation. Secondary antibodies which bind to primary antibodies may be labeled with fluorescent molecules that permit separation of cells in a fluorescence activated cell sorter. Alternatively, metallic microbeads may be linked to primary or secondary antibodies. In this manner, magnets may be used to isolate these antibodies and the cells bound to them.

To achieve positive or negative selection, the heterogeneous cell population is incubated with primary antibodies for a time sufficient to achieve binding of the antibodies to the antigen on the cell surface. If the primary antibodies are labeled, separation may occur at this step. If secondary antibodies are employed, then the secondary (anti-primary) antibodies are incubated with the cells bound to the primary antibodies for a time sufficient to achieve binding of the secondary antibodies to the primary antibodies. If the secondary antibody has a fluorescent label, then the cells are sent through a fluorescence activated cell sorter to isolate the labeled antisera bound to the desired cell. If the secondary antibody has a magnetic label, then the selected cell with the primary antibody and secondary antibody-labeled microbeads form a complex that when passed through a magnet remain behind while the other unlabeled cells are removed along with the cell medium. The positively labeled cells are then eluted and are ready for further processing. Negative selection is the collection of the unlabeled cells that have passed through the magnetic field.

MACS Technology (Miltenyi Biotec) is an example of what may be used in the present invention and is based on the use of MACS MicroBeads, MACS Columns and MACS Separators. This technology is known to one of ordinary skill in the art. MACS MicroBeads are superparamagnetic particles that are coupled to highly specific monoclonal antibodies. They are used to magnetically label the target cell population. They are approximately 50 nm in size, not visible with light microscopy, biodegradable, and gentle on cells.

As the MicroBeads are extremely small, the use of a high-gradient magnetic field is required to retain the labeled cells. The MACS Column Technology is specifically designed to generate this strong magnetic field while maintaining optimal cell viability and function. By using a MACS Column with a coated, cell-friendly matrix placed in a permanent magnet, the MACS Separator, the magnetic force is now sufficient to retain the target cells labeled with a minimum of MicroBeads. By simply rinsing the column with buffer, all the unlabeled cells are washed out thoroughly, without affecting the labeled or unlabeled cell fractions, thus ensuring optimal recovery. By removing the column from the magnet, the labeled fraction can be obtained. With MACS Technology both the labeled and the unlabeled fraction are now highly pure, and an optimal recovery of the cells is guaranteed.

Isolation of B cells from heterogeneous cell populations and stem cell populations involves the negative selection process in which the marrow first undergoes red cell lysis by placing the bone marrow in a hypotonic buffer and centrifuging the red blood cells out of the buffer. The red blood cell debris remains in the supernatant which is removed from the test-tube. The bone marrow derived cells are then resuspended in a buffer that has the appropriate conditions for binding antibody. Alternatively, the bone marrow can be subjected to a density gradient centrifugation. The buffy coat layer containing the bone marrow derived cells is removed from the gradient following the centrifugation. The cells are washed and resuspended in the antibody binding buffer and is then incubated with primary antibodies directed toward stem cells, T cells, granulocytes and monocytes/macrophages (called lineage depletion) followed by positive selection using antibodies toward B cells.

In the present application anti-CD3 and anti-CD4 antibodies were used for T cells, anti-CD11b/c antibodies were used for monocytes/macrophages, anti-granulocyte antibodies were used for granulocytes, and c-kit antibodies were used for stem cells. Then, for positive selection, CD45RA antibodies were used for rat B cells.

In another embodiment, the primary antibodies are attached to a matrix and the cells are incubated with this matrix. Those cells with surface antigens recognized by the primary antibodies are bound to the primary antibodies while other cells without these surface antigens are not. In one embodiment, this matrix is contained in a syringe and acts as an affinity column. Bound cells are subsequently eluted from the column and may be used at this stage or subjected to a further purification step in another affinity column containing the same primary antibody or another primary antibody that recognizes another surface antigen on the target cell. Elution of bound cells may occur using techniques such as adjustment of pH, addition of a buffer of altered tonicity, salt or other techniques useful for interfering with antigen-antibody binding known to one of ordinary skill in the art. These affinity columns may be used for positive selection, negative selection or both, in order to obtain a relatively pure preparation of B cells for administration to the injured tissue.

Pretreatment of B Cells

B cells may be optionally pretreated by exposing them to hypoxic conditions in order to increase B cell adhesion to mesenchymal cells and to enhance B cell activity. This pretreatment can be achieved once the bone marrow is harvested and the B cells isolated as described earlier. Prior to delivery of the B cells, the B cells are incubated within a closed system containing a sub-physiologic level of oxygen.

Number of Cells for Administration

The number of cells to be administered will be related to the area or volume of injured tissue to be treated, the method of delivery, and in some cases the species to be treated. For example, rats have relatively small hearts and so the myocardium is much smaller and thinner than larger species such as dogs, pigs and humans. The number of cells used in rat studies is described in Example 1 and in the Figures. The injections in the rat study reported herein, consisted of 4 injections of 20 ul each. Thus a total of $10^6$ cells in 80 ul was injected into rat hearts weighing approximately 1.2 gm at termination.

One non-limiting range of B cell number for administration is $10^4$ to $10^{14}$ B cells, depending on the volume of infarcted tissue to be treated, and in some cases the species to be treated. Other ranges include $10^5$ to $10^{12}$ B cells and $10^6$ to $10^{10}$ B cells.

Individual injection volumes can include a non-limiting range of from 1 ul to 1000 ul, 1 ul to 500 ul, 10 ul to 250 ul, or 20 ul to 150 ul. Total injection volumes per animal range from 10 ul to 10 ml depending on the species, the method of delivery and the volume of the tissue to be treated.

For administration to larger animals higher number of cells in larger volumes may be employed. In a study performed using pig hearts, a total of $10^8$ unfractionated bone marrow cells was administered in 16 injections of 100 ul each in 1.6 ml total volume. Human patients will be treated with an effective amount of B cells which may be similar numbers of cells and similar volumes of cells as described above for use in pigs, but may be higher or lower.

Site and Method of Administration

B cells may be administered using any method that delivers the B cells to the injured tissue or the tissue surrounding the injury. B cells may be administered through injection via a syringe and appropriately sized needle.

B cells may also be administered through a cannula placed within a body cavity, a vessel, a duct, a lumen of an organ, within an organ, a space surrounding an organ such as pericardial or pleural spaces, or intrathecally. B cells may also be applied topically for surface wounds or directly to injured tissue during surgery. In one embodiment, B cells may be administered through an intraarterial cannula to injured tissue supplied by the artery.

In the present method the cells are administered directly into the injured tissue in one or more injections. Cells may also be administered into the border zone surrounding injured tissue. In the case of infarcted cardiac tissue, B cells may also be administered directly into the infarcted cardiac tissue and into the border zone surrounding the infarcted cardiac tissue. In another embodiment, cells may be administered into less than adequately perfused tissue which is not infarcted. It is to be understood that the distance or spacing between injections into the tissue will vary depending on the size of the area to receive cells and the species. For example, in rats the heart is small and the injections of cells are spaced about 1 mm to 2 mm apart.

In pigs or humans with much larger hearts than rats, cells are optionally administered into the myocardium using the Boston Scientific Stiletto™ myocardial injection catheter with intracardiac echocardiography (ICE) guidance. The myocardial injection catheter is introduced via femoral artery cutdown and used according to the manufacturer's instructions. In one embodiment, the total number of cells is delivered to the tissue in 16 injections (8 injections to the ischemic region and 8 injections into border zone region) of 100 μl volume containing no less than $1 \times 10^8$ cells in a total volume of about 1.6 ml. Such treatment may comprise injections of freshly isolated bone marrow cells into the injured area or border zone of the injured area.

Another method of the present invention is to give agents that cause B cells to mobilize into the circulation and/or to home to the targeted tissue. These methods assist in achieving increased levels of B cells at the targeted tissue without the need for harvest and reinjection. For example, CXCL13 is a known B cell chemokine that could be delivered to the targeted tissue along with a B cell mobilizing agent to augment presence of B cells in the targeted tissue. Another technique utilizes a chemokine antagonist that lowers the amount of chemokines contained within the targeted tissue to a level that is compatible with B cell activity. Another method is to implant a substrate or device such as an intravascular stent into or near the targeted tissue wherein the substrate or device is coated with a matrix containing an antibody which reacts with a B cell antigen thereby localizing and concentrating B cells at the implant site. In this method, the number of circulating B cells could be augmented through the harvest from another organ such as bone marrow, isolated, concentrated and delivered back to the patient's blood system.

Another technique utilizes other methods to condition B cells in vivo to promote adherence of the B cell to the surface of the implanted substrate, device or injured tissue in order to concentrate or increase their levels at the targeted tissue. In this technique, a substance could be delivered systemically, such as a bifunctional antibody, that adheres to surface antigens on B cells, for example the CD19 surface antigen, and also adheres to the implant surface or injured tissue to cause B cell localization at that site. This approach can be used in conjunction with administration of autologous B cells harvested from the animal or human. This approach can also be used in situations wherein autologous B cells are not harvested from the animal or human but when an increase of endogenous B cells at the injured tissue is desired. For example, administration of such a substance to the animal or the human with the injured tissue can bind to available B cells, such as circulating B cells, and also to the site of the injured tissue, thereby increasing the number of B cells at the site.

Method of Administration to Infarcted Cardiac Tissue

Preferably, the injections are made through a small gauge needle, preferably in the range of 32 gauge to 21 gauge, or in a range of 30 gauge to 23 gauge. The needle size may vary depending on the type, depth, and thickness of the tissue to be injected. For example in the rat, a 27 gauge needle was employed. In humans, various gauges of needles or catheters may be used. The Boston Scientific Stiletto™ myocardial injection catheter which utilizes a 27 gauge needle may be employed. In one embodiment, the injections are made through the pericardium into the infarcted region of the myocardium.

All of the procedures associated with the harvest and injection of cells are performed using sterile technique. Areas of infarction are visualized using echocardiography and the injections are performed using both fluoroscopy and intracardiac echocardiographic guidance. Another technique includes the use of trans-esophageal echo. Another technique includes the use of visual, tactile and anatomical landmarks for transcutaneous direct injection. Yet another technique reported is intravenous delivery which requires no visualization technique. If intra-coronary infusion is used, fluoroscopy is the preferred method.

In one method of cell delivery, an occlusive balloon is placed proximal to the infarcted tissue to deliver cells. A common device is a PTCA balloon that is inflated using low pressure and the cells are delivered via the wire lumen. The advantage is to temporarily stop flow to enhance cell adhesion and uptake within the targeted tissue.

In another embodiment, the injections are made through vascular catheters equipped with injection means. Such catheters are guided by one of skill in the art, such as an interventional cardiologist, a veterinarian, or another trained assistant. The catheter is directed to the infarcted region through the vascular system leading to the coronary arteries using visualization techniques, including but not limited to the intracardiac echocardiography guidance (ICE) and NOGA mapping (maps electrical signal conductance) as known to one of ordinary skill in the art. NOGA is a commercial name for a catheter system that utilizes a three dimensional (3D) mapping system combined with an ECG detection algorithm that reportedly correlates the signal to myocardial viability.

Carriers

The B cells to be administered are suspended in a pharmaceutically acceptable carrier such as pharmaceutically acceptable fluid. Such fluids include but are not limited to saline, cell culture medium and plasma. Additional pharmaceutically acceptable carriers include scaffolds, matrices, glues, gels and other tissue retention carriers with or without cytokines and growth factors.

Timing of Administration of B Cells

The timing of administration of B cells to injured tissue will vary depending on the condition of the patient. In general, B cells are administered in hours, days, weeks, months or years after an injury. The present invention may also be used to treat chronic conditions in which case administration schedules will be determined by the physician or veterinarian. Cells may be administered to patients one or more times following injury depending on the severity of the patient's condition and the recovery of function following administration of B cells.

Combination Therapy

In addition to the use of cells alone for the treatment of tissue injury, the present invention contemplates the combination therapy of cells with other substances. Such substances include, but are not limited to, substances which facilitate restoration of tissue function or the function and/or survival of the cells to be administered (delivery success). Such substances include but are not limited to the following: growth factors VEGF, FGF, IGF-1; nitric oxide donors such as nitroglycerin; COX-2 inhibitors; anti-inflammatories; HMG coreductase inhibitors; statins; angiotensin converting enzyme (ACE) inhibitors, thrombin, chemokines including but not limited to CXCL12, CXCL13, CCL19, CCL21, CCL25, CXCL9, and CXCL10; NSAIDS, chemokine antagonists, thrombin, extracellular molecules, integrin ligands including but not limited to MADCAM1 (mucosal addressin cell-adhesion molecule 1) and VCAM1 (vascular cell-adhesion molecule 1); interleukin-4; substances altering vascular perfusion such as vasodilators, osmotic agents, anticoagulants, acid/base modifying agents, surfactants, or combinations thereof. These substances may be administered in dosages and using regimens known to one of ordinary skill in the art.

Treatment of Injured Tissue

B cells may be administered to any injured or otherwise compromised tissue. Preferably, B cells are administered to tissue following any injury. Tissue injury may result from many different causes. Diseases or conditions leading to injury of tissue that may be treated with the method of the present invention include but are not limited to the following: tissue injury following ischemia or hemorrhage, organ transplant, trauma, surgery, inflammation, infection, cardiovascular disease, heart disease including acute infarction, chronic ischemia and myocardium with less than desired perfusion; peripheral vascular disease; decreased perfusion due to diabetes; kidney disease including chronic renal ischemia; congestive heart failure; and, ischemic stroke.

B cells may be administered directly into the injured tissue and/or may be administered into tissue surrounding the injury. In one embodiment, B cells may be administered into infarcted myocardium or into myocardium surrounding the infarcted tissue. Injection of cells into the ischemic cardiac tissue enhances cardiac function following infarction. The methods of the present invention can be used for lessening the decline in cardiac function following an ischemic episode. Further, the methods of the present invention improve cardiac function following ischemia. This improvement in cardiac function provides a better quality of life or longevity for such individuals, enabling them to engage in physical or other activities that might be otherwise proscribed or contraindicated. By restoring cardiac function following ischemia, use of the method of the present invention decreases the chance of cardiac arrest following an episode of cardiac ischemia.

The present method may be used to treat other conditions related to poor perfusion or less than normal blood flow and oxygenation, including but not limited to the following: peripheral vascular disease, decreased tissue perfusion in diabetics for example in tissue located in the extremities, decreased cardiac perfusion in patients with atherosclerosis of one or more coronary arteries, decreased cardiac perfusion in patients undergoing bypass surgery or another cardiac procedure, renal disease including ischemic renal diseases, decreased cranial perfusion in patients with atherosclerosis of one or more carotid arteries or branches thereof, or with atherosclerosis of one or more vertebral arteries or other arteries in the cerebrovascular circulation, temporary ischemic episodes, stroke, occlusion of vessels due to trauma, a mass or any other cause.

A System for Treating Injured Tissue in a Human

The present invention includes a system for treating injured tissue in a human. This system comprises several steps comprising: obtaining a sample containing B cells from the human with the injured tissue; purifying the sample to produce a relatively pure population of B cells; combining the relatively pure population of B cells with a pharmaceutically acceptable carrier to produce a composition; and, administering the composition to the human with the injured tissue in an amount effective to treat the injured tissue in the human.

In this system, equipment and reagents are employed to achieve the goal of treating the injured tissue in the human as described elsewhere in this application.

Kits

The present invention includes kits for use in isolation of human B cells. These kits are useful in the isolation of B cells from heterogeneous cell populations. Instructions are provided for use of the kit.

Kits may employ positive selection techniques, negative selection techniques, or a combination thereof, to isolate a relatively pure population of B cells from a heterogeneous mixture of cells. Positive selection techniques employ antibodies that recognize antigens on the B cells. Antibodies that recognize antigens B cells include but are not limited to antibodies that bind CD19, CD19+, B220+ or B cell receptor (Igαβ)+.

A non-limiting example of a kit for positive selection of B cells is presented in Example 10. Negative selection techniques employ antibodies that recognize antigens on the cells to be separated from the B cells. A non-limiting example of a kit for negative selection of B cells is presented in Example 11. Negative selection techniques employ antibodies that include but are not limited to antibodies that bind the following human cell surface antigens: CD2, CD3, CD14, CD16, CD36, CD43, CD56, and glycophorin A that reside on T cells, NK cells granulocytes, monocytes/macrophages, and erythrocytes.

Generally speaking, kits include a separation chamber, optionally including: a centrifugation chamber; a collection bag connected to the separation chamber; means to connect the collection bad to the separation chamber such as connection units, connection lines, and luers; a manifold, antibodies that recognize antigens on B cells or antibodies that recognize antigens on non B cells, or both; separation means such as a filter or a column; and, a collection vial for the isolated B cells.

Antibodies may optionally be linked to magnetic beads as known to one of ordinary skill in the art. Kits may employ affinity columns in which antibodies used for positive or negative selection are suspended in a medium such as a chromatography medium known to one of ordinary skill in the art, for example Sepharose. Such antibodies have been described elsewhere in this application. Such affinity columns may act as separation chambers. Another separation chamber is a tube coated with antibodies on its inner wall.

Kits may also employ materials such as polystyrene, polypropylene, stainless steel, nitinol, rubber or other materials known to bind to cells.

Kits optionally contain buffers for elution of bound cells or cells trapped by a filter, a buffer for resuspending the isolated B cells before administration to the human. Filters that trap cells and separate cells from viruses or other undesired plasma components may also be employed.

The following examples will serve to further illustrate the present invention without, at the same time, however, constituting any limitation thereof. On the contrary, it is to be clearly understood that resort may be had to various embodiments, modifications and equivalents thereof which, after reading the description herein, may suggest themselves to those skilled in the art without departing from the spirit of the invention.

Example 1

Recovery of Cardiac Function Following Ischemia in Rats

Bone marrow cells were harvested from donor rats and separated into stem cell and B cell populations and directly injected into infarcted recipient rat hearts. These animals are extremely in-bred and are often used in this way to substitute for the human autologous situation. Baseline and two-week follow-up echocardiography was performed to measure left ventricular end systolic and diastolic diameter and percent shortening (percent shortening is the heart's short-axis "stroke diameter" (difference between end-diastolic and end-systolic diameters) divided by the diameter in diastole. This measurement accurately reflects global left ventricular function and is highly correlated with ejection fraction.

A normal heart with normal wall motion and contractility will have a greater percent shortening value compared to a dysfunctional heart in which contractility is impaired and shortening is reduced). Hemodynamic indices including positive dP/dT was measured during the 2-week follow-up procedure. Hearts were harvested and subjected to histological staining for determination of infarction area and capillary density.

Figure 2:
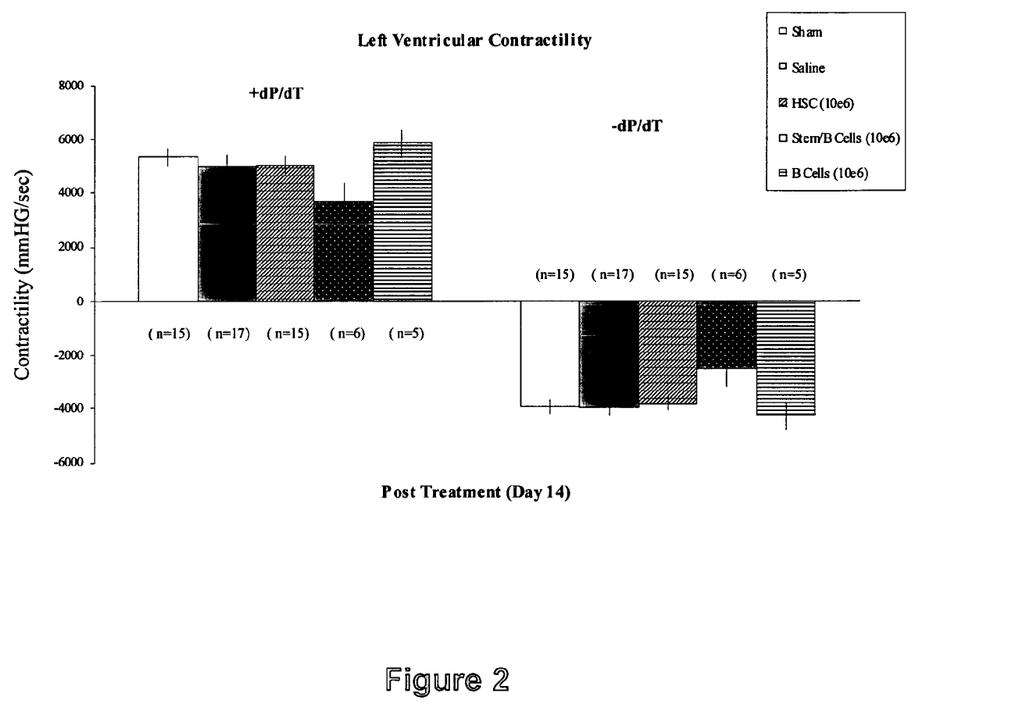

The co-injection of stem cells and B cells had a deleterious effect on left ventricular function compared to injection of B cells alone as seen with the positive dP/dT measurement in FIG. 2. The deleterious effect of stem cells combined with B cells is one possible explanation for the negative results reported using whole bone marrow.

Figure 3:
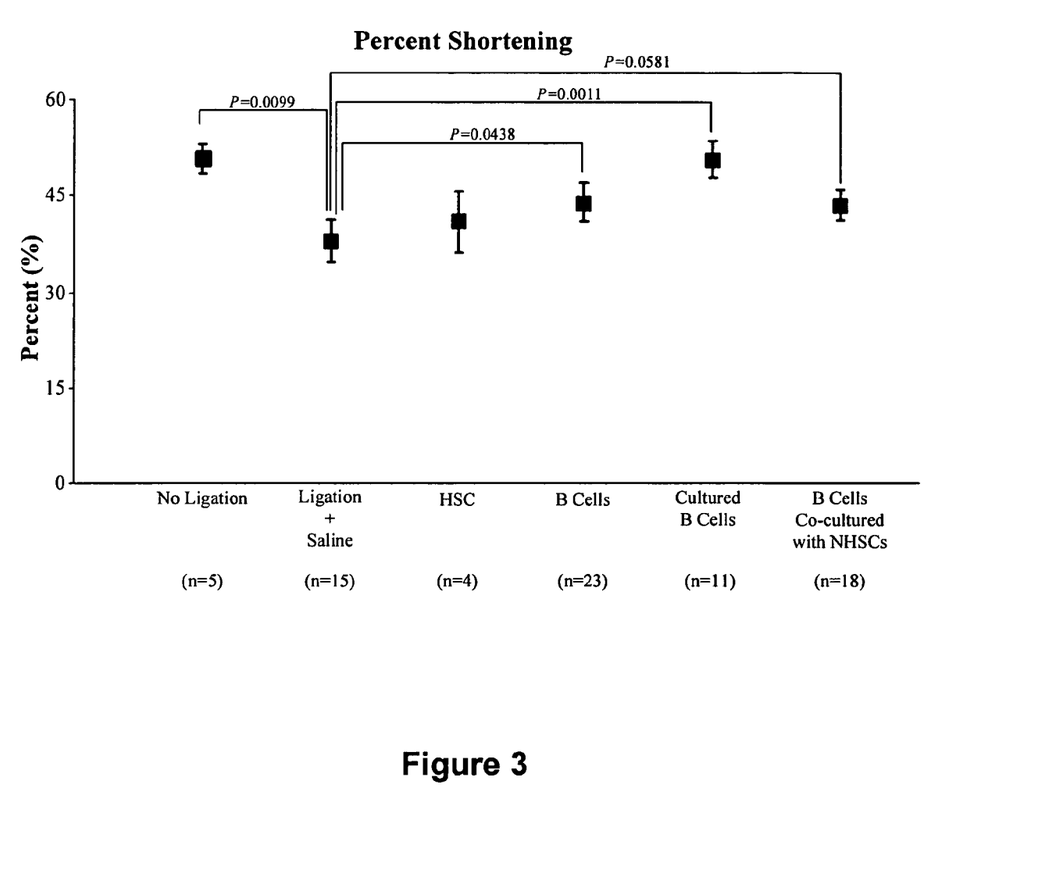

The results indicate that an improvement in cardiac function occurred when relatively pure populations of B cells were injected as determined by percent shortening (see FIG. 3). This improvement was unique to B cells since administration of HSCs alone did not enhance function nor did other cells contained within the bone marrow (data not shown). Our studies investigating B cell mechanism of action on cardiac ischemic injury repair indicate that B cells both increase cellular proliferation and decrease cellular apoptosis. Taken together, these data demonstrate that administration of relatively pure populations of B cells provided a functional and anatomical recovery in the heart.

Animals: Male Sprague-Dawley rats (about 250-350 g body weight) were anesthetized with isoflurane (3.5% with 0.8 L oxygen), subjected to orotracheal intubation and ventilated with positive pressure (Topo, Kent Scientific). Anesthesia was maintained using isoflurane (3.5% with 0.5 L oxygen). Animals were then placed on a controlled heating pad maintained at 37° C. (Gaymar T/Pump). ECG monitoring was performed in order to verify ST elevation associated with left ventricular infarction.

Figure 1:
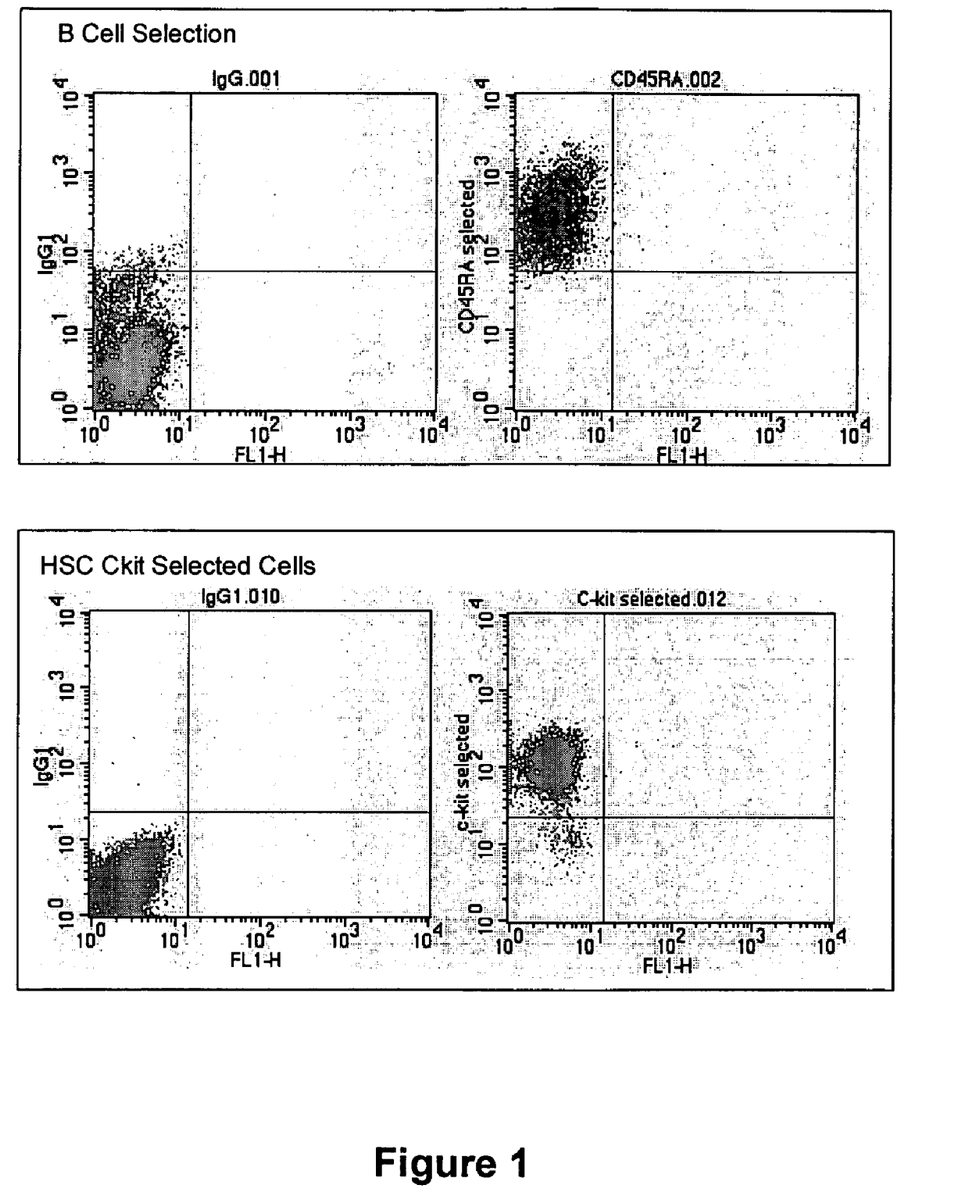
FIG. 1: Depicts flow cytometric separation of the ckit+ hematopoietic stem cells (HSC) and CD45RA positively selected cells (B cells).

Bone marrow cell separation: Donor Sprague-Dawley rats were anesthetized with 80 mg/kg of ketamine, 2.0 mg/kg of xylazine then euthanized via exsanguination. Femurs and tibias were harvested and the shafts flushed with Dulbecco's modified essential medium (DMEM) supplemented with 2% fetal bovine serum (FBS) and gentamicin (2 mg/ml). The bone marrow (BM) was collected and diluted 1:2 with Dulbecco's phosphate buffered saline (DPBS) and layered onto a Ficoll density gradient (Histopaque-1077, Sigma, St. Louis Mo.). The buffy coat was collected and washed 3 times with DPBS then incubated with various antibodies and subjected to the Miltenyi cell separation procedure. B cells were selected either by lineage depletion using antibodies including but not limited to CD3 (T cells), CD8 (T cells), Granulocyte (neutrophils), CD11b/c (monocytes) and ckit (HSCs) antibodies followed by positive selection with CD45RA antibody or by positive selection with CD45RA antibody alone. Hematopoietic stem cells (HSCs) were selected by lineage depletion with the antibodies mentioned above followed by positive selection with ckit antibody while non-hematopoietic stem cells were selected by lineage depletion with the antibodies mentioned above plus CD45 antibody followed by positive selection with antibody directed against ckit. Purity of cell populations were determined using flow cytometric analysis. In the present application, relatively pure means at least 80% pure, 85% pure, 88% pure, or even higher degrees of purity such as at least 90% pure, preferably at least 95% pure, preferably at least 97% pure, or preferably at least 98% pure. Once populations were separated and purity confirmed by fluorescence activated cell scan analysis (FIG. 1), cells were either kept at or 37° C. until the day of myocardial injection or immediately injected into the animals. On the day of cell injection, HSCs, NHSCs and B cells were washed with DPBS, and resuspended in sterile saline for injections.

Induction of myocardial infarction: After surgical preparation and drape, using sterile technique and equipment, a left lateral thoracotomy was performed and a rib-spreading chest retractor was inserted. The left anterior descending artery (LAD) was isolated and ligated using sterile 6-0 prolene and the artery ligation was confirmed by the visual change of color, or blanching in the area of infarction along with an ECG change of ST elevation. Sham animals had the same procedure however the ligature around the LAD was left untied. Another control group was the sham group plus administration of B cells. All groups are shown in the figures.

The ST level was measured relative to the PR interval. With tachycardia or ischemia the direction changes, as does the ST amplitude. Pathological processes that cause ST elevation shift the entire vector from its long axis of the heart orientation and move it through the area of transmural ischemia (infarction or spasm).

Bone marrow cell treatment: After ligation of the LAD and confirmation of myocardial infarction, animals received a total of $10^6$ cells (except for the one case shown in FIG. 2 in which $5 \times 10^6$ B cells alone were injected) in 4 injections of 20 ul (about 250,000 cells per injection, 12,500 cells per ul) directly into the infarcted region are spaced about 1 mm to 2 mm apart, using a Hamilton syringe with a 27 gauge needle. Injections were performed by the surgeon and done by hand, directly into the myocardium. Control animals received saline. The chest was closed using sterile suture (4-0 Vicryl) and the animal was allowed to recover from the surgical procedure.

Cell Culturing Method

In another aspect of these experiments, animals received the B cells that have been cultured overnight at 37° C. In addition to culturing separately, both stem cells and B cells were co-cultured with the B cells placed on top of a transwell filter (0.4 urn pore size) and the stem cells below the transwell filter. Cells were seeded at a 1:1 ratio of B cells to stem cells and cultured overnight in DMEM containing 10% FBS with 1% penicillin and 1% streptomycin. Either B cells or stem cells were collected the next day and prepared for injections.

When B cells were co-administered with stem cells, the total number of cells administered was $10^6$. Stem cells and B cells were mixed together and the slurry of cells was injected.

Echocardiographic evaluation: The echocardiographic procedure was performed immediately before opening the chest and repeated two weeks later at sacrifice. Initially, a 2-dimensional short-axis view of the left ventricle (LV) was obtained at the level of the mid-papillary and apical levels. After optimizing gain settings and ensuring that the image is on axis, M-mode tracings were recorded through the anterior and posterior LV walls. The M-mode echocardiogram provides a one-dimensional view (depth) into the heart. The M-mode images represent echoes from various tissue interfaces along the axis of the beam. These echoes, which move during the cardiac cycle, are swept across time on the oscilloscope/recording, providing the dimension of time. Thus, the lines which are seen on the recordings correspond to the position of the imaged structures in relation to the transducer and other cardiac structures at any point in time. The M-mode echocardiograph uses a high sampling rate and can provide more accurate images of cardiac borders. Measurements of cardiac dimensions and motion throughout the cardiac cycle are often more accurately obtained from M-mode tracings. This orientation for M-mode tracings was chosen to allow delineation of wall thickness and motion in infarcted and noninfarcted regions. The results were recorded on VHS tapes, and the M-mode tracings analyzed. LV mass was been calculated automatically by the internal software using a cube formula. Relative anterior wall thickness, relative posterior wall thickness, and LV internal dimensions were measured from at least three consecutive cardiac cycles. Endocardial fractional shortening and mid wall fractional shortening was used as indices to estimate LV systolic function.

Restudy and Termination: After two weeks, animals were sedated and intubated as described above. A cutdown was performed to the cervical area and the right carotid artery was dissected. A 2 Fr Millar catheter (SPR-612 or SPC 320; Millar Instruments, Houston, Tex.) was inserted into the LV through the right carotid. Pressure of the LV was recorded (dP/dT) along with aortic pressures. Animals were sacrificed with KCl and the heart removed, wet weight recorded and processed for histological evaluation.

Histological tissue processing: After sacrifice, the hearts were briefly rinsed with saline perfusion and then fixed using 4% paraformaldehyde via a cannula through the aorta. Following fixation, the tissue were processed one of two ways for analysis of cardiac cell apoptosis or analysis of cardiac cell proliferation; 1) paraffin-embedded 2) embedded in tissue freezing-medium.

Figure 4:
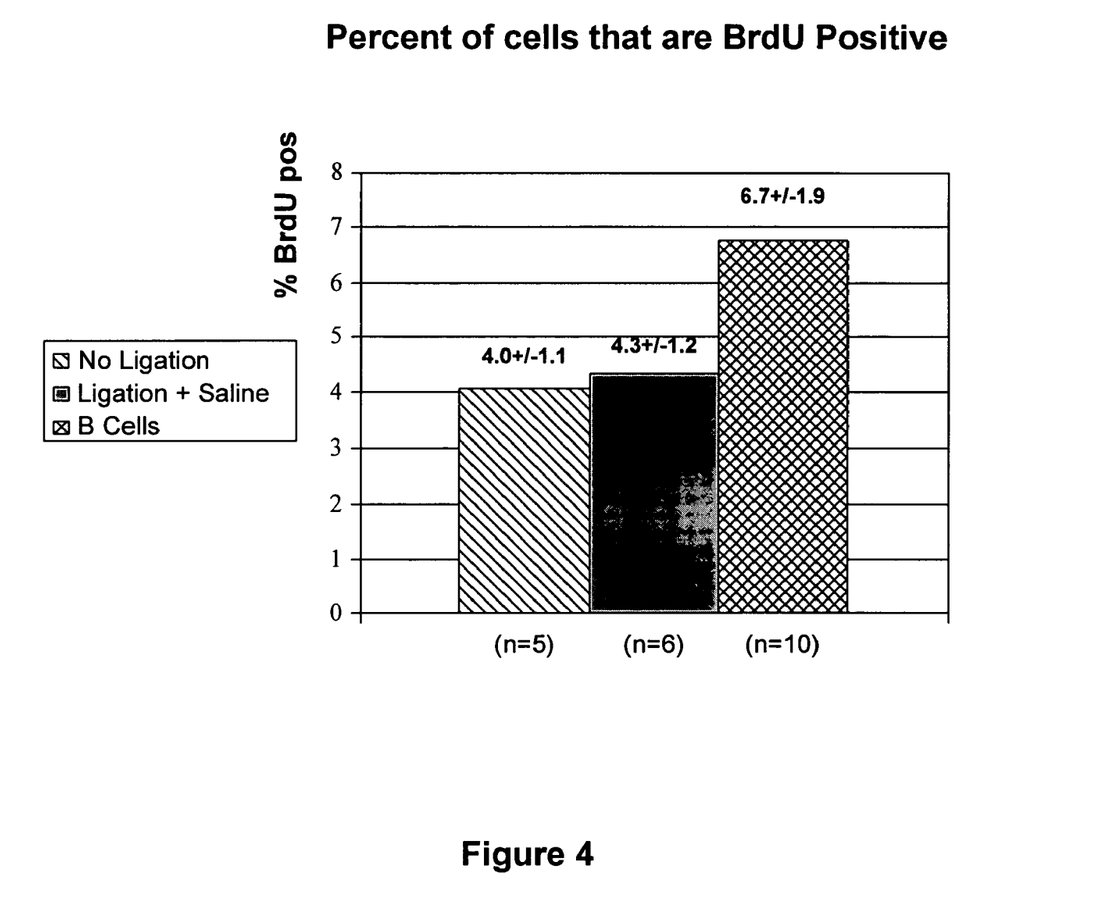
FIG. 4: Cardiac cell but not necessarily cardiomyocyte proliferation is up regulated following B cell injection post myocardial infarction. Animals were implanted with a BrdU pellet at time of infarction and cell injection. After 2 weeks, animals were euthanized and hearts processed for assessment of BrdU incorporation into the nuclear DNA of proliferating cells. Positive cells were identified using antibodies directed against BrdU. The percentage of cells staining positive for BrdU was determined by comparison to the total number of cells quantitated within the peri-infarct domain. Significance of the data was assessed using the Student t-test, two-tailed.

Determination of cardiac cell proliferation: Animals were implanted with a bromodeoxyuridine (BrdU) pellet at the time of the myocardial infarction and cell injection procedure. After 2 weeks, animals were euthanized and hearts processed for BrdU assessment. BrdU positive cells are stained with labeled anti-BrdU antibodies and all nuclei are counterstained with Hematoxylin. All images were taken using 40× objective lens and positive cells were quantitated. Few BrdU-positive cells were detected in sham (no ligation) operated animals. BrdU proliferating cells were observed in ligation plus saline treated animals, though more BrdU staining was found in the B cell treated hearts (FIG. 4).

Figure 5:
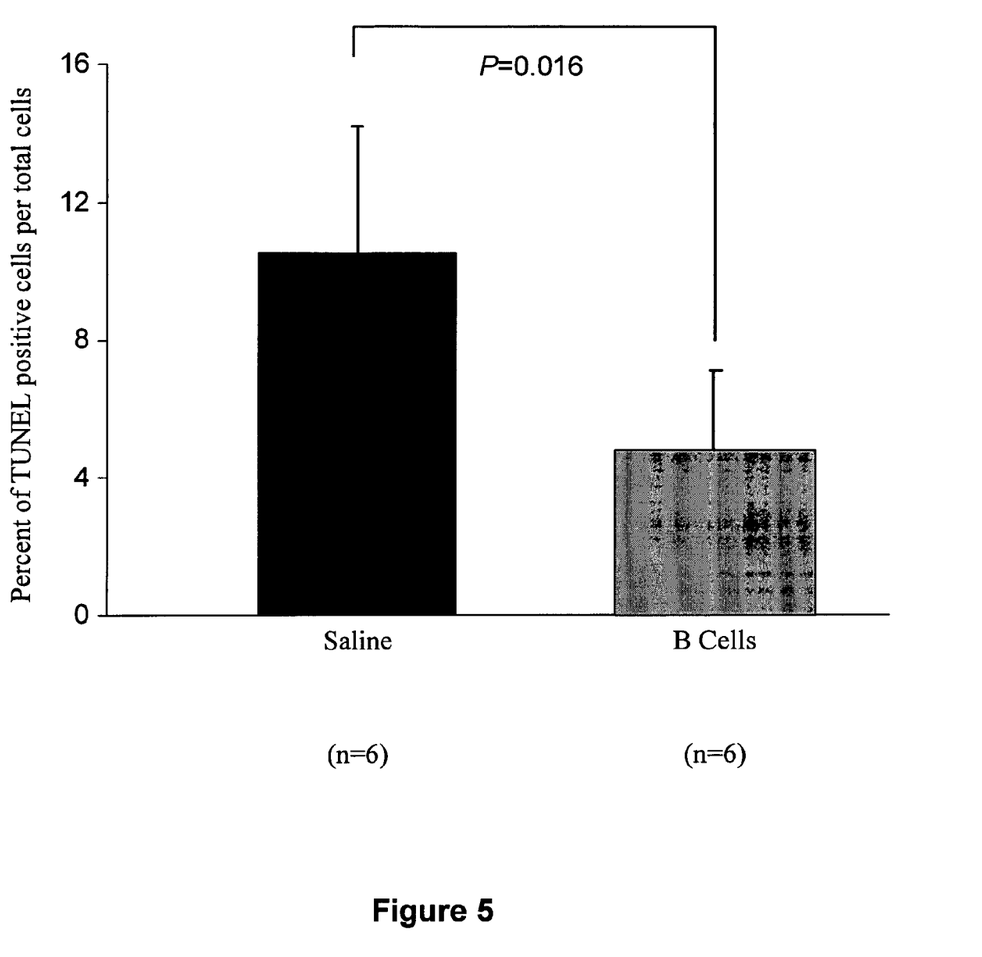
FIG. 5: B cells preserve cardiac tissue following ischemic injury by reducing apoptosis. Assessment of cellular apoptosis was performed using the TUNEL assay. Animals underwent a ligation operation followed by either saline or B cell injection (1 million cells). Animals were euthanized at 48 hours after surgery and hearts were processed for evaluation of apoptosis. Apoptotic cells within the peri-infarct domain were quantitated by comparison to the total number of cells quantitated in the peri-infarct domain. Significance of the data was assessed using the Student t-test, two-tailed.

Determination of cardiac cell apoptosis: Animals underwent sham (no ligation) operation or ligation with B cell injections. Animals were euthanized at 48 hours after surgery. Hearts were processed for histological evaluation of apoptosis using the TUNEL assay. Apoptotic cells are stained with the stable chromogen, diaminobenzidine while all nuclei are stained with Hematoxylin. All images were taken using 40× objective and positive cells were quantitated (FIG. 5).

Statistics—Hemodynamic Data

T-tests were run and significance evaluated based on a two tailed test at p<0.05. Analysis of variance (ANOVA) was also performed on all the different cardiac functional measurements and if differences in the Least Squared Means between groups were detected, a Tukey post-hoc analysis was performed and the p-value given.

The results indicate that an improvement in cardiac function (see changes in percent shortening FIG. 3) occurred when relatively pure populations of B cells were injected. However, when stem cells and B cells were co-administered, no improvement was observed. (FIGS. 2, 3). Freshly isolating the bone marrow cells immediately before injection and culturing produced the greatest improvement in cardiac function following injury (FIG. 3). Studies investigating B cell mechanism of action on cardiac ischemic injury repair indicate that B cells both increase cellular proliferation and decrease cellular apoptosis. Taken together, these data demonstrate that administration of relatively pure populations of B cells provided a functional and anatomical recovery in the heart.

Example 2

Treatment of a Human Patient Following Myocardial Infarction

A 55 year old male visits his cardiologist complaining of angina. An arteriogram reveals 90% blockage in the left anterior descending coronary artery. During a treadmill test the patient suffers an acute myocardial infarction and survives. Subsequent-tests reveal that a portion of the left ventricular myocardium is damaged from the infarction.

The patient undergoes open-chest surgery to bypass the left anterior descending coronary artery with a saphenous vein graft. During the surgery, the infarcted area is visualized. Approximately 200 ml of bone marrow are aspirated from the iliac crest and processed to separate out the subpopulation of CD19+ cells. Sixteen injections of these bone marrow derived B cells at a concentration of about 100 million cells per 1.6 ml are made directly into the ischemic myocardial tissue in a total volume of about 100 ul per injection, using a 27 gauge needle.

Following completion of the surgery, the patient is monitored during the next several months. The ischemic area which received injections of CD19+ cells shows improvement in vascularity and contractile function during this period.

Example 3

Treatment of a Human Patient Following Myocardial Infarction

A 62 year old female patient with an infarction of the right coronary artery suffers ischemic damage. B cells are obtained from the patient's bone marrow and cultured overnight before administration of the cells (1000 ul containing 120 million cells). The patient is placed on a regimen of drugs using a protocol similar to what is provided to a post infarction patient by one of ordinary skill in the art. The next day, the patient's coronaries are cannulated with a guide catheter introduced at the groin via the femoral artery. A PTCA balloon is introduced through this catheter into the coronaries and inflated with sufficient pressure to occlude coronary blood flow. The PTCA wire is removed and the cells are then injected through the balloon's wire lumen and delivered distal to the inflated balloon. After approximately 90 seconds, the balloon is deflated and the procedure is concluded. Following completion, the patient is monitored during the next several months. The ischemic area which received injections of CD19+ cells shows improvement in vascularity and contractile function during this period.

Example 4

Treatment of a Human Patient Following Myocardial Infarction

A 35 year old obese male with an infarct in the left cardiac ventricle is indicated for a PTCA instead of a surgical bypass. The B cells are harvested from the iliac and delivered with a trans-femoral device that crosses the aortic valve, engages the left myocardium, deploys a needle that allows for injection of the cells directly into the myocardium. Prior to injection, the B cells are mixed with a matrix substance such as fibrin sealant, biopolymer or collagen that enhances cell retention, survivability and effectiveness. In addition, stents that are placed in the proximity of the infarct are coated with a matrix and an antibody which reacts with a B cell antigen that preferentially attracts and retains these cells.

Example 5

Treatment of a Human Patient with Congestive Heart Failure Following Ischemia

A patient suffers from congestive heart failure believed to be caused by ischemia. The procedure begins with harvesting between 50 and 500 ml of bone marrow from the patient's iliac crest and processed with a kit (a closed-bag system) that isolates CD19+ cells in a relatively pure formulation. Prior to delivery of these cells, the patient's coronary arteries are cannulated with a diagnostic catheter common to the PTCA industry. Delivery of the purified cells into the artery is achieved with injection of the cells into the diagnostic catheter. An improvement in cardiac function is measured days after administration of the cells.

Example 6

Treatment of a Human Patient with Damage to the Central Nervous System Following Hemorrhagic Stroke A patient suffers a hemorrhagic stroke due to bleeding from an arteriole branching from the left middle cerebral artery. The bleeding in the vicinity of the postcentral gyrus threatens motor function. The procedure begins with harvesting between 50 and 500 ml of bone marrow from the patient's iliac crest and processed with a kit (a closed-bag system) that isolates approximately 200 million CD19+ B cells in a relatively pure formulation. Prior to delivery of these cells, the patient's left internal carotid artery is cannulated with a diagnostic catheter commonly known to interventional surgeons. A device is deployed into the left internal carotid artery and threaded to the origin of the middle cerebral artery. The purified B cells suspended in a pharmaceutically acceptable carrier are slowly injected into the middle cerebral artery, and are carried by blood flow to the site of hemorrhage. An improvement in motor function is measured days after administration of the B cells.

Example 7

Treatment of a Human Patient with Damage to the Central Nervous System Following Hemorrhagic Stroke A patient suffers a hemorrhagic stroke due to bleeding from an arteriole branching from the posterior cerebral artery. The bleeding in the vicinity of areas 18 and 19 of the occipital cortex threatens visual function. The procedure begins with harvesting B cells from the patient's blood and processing with a kit (a closed-bag system) that isolates CD19+ B cells in a relatively pure formulation. Prior to delivery of these cells, the patient's skull is stabilized in a stereotaxic device and a craniotomy in the occipital bone is performed using techniques commonly known to neurosurgeons. The dura is pierced and a needle connected to an injection syringe containing over 100 million B cells in a pharmaceutically acceptable carrier is introduced into area 18 surrounding the clot using a micromanipulator. B cells are then slowly injected in a volume of 1-5 ul. This procedure is repeated for injection into area 19 surrounding the clot. An improvement in visual function is measured days after administration of the B cells.

Example 8

Treatment of a Human Patient with Damage to the Kidneys Following a PTCA Procedure A patient undergoes a routine procedure to revascularize the myocardium using PTCA techniques including the use of contrast medium for fluoroscopic visualization. The patient's kidneys react to the contrast medium causing portions of the kidney to fail referred to as contrast induced nephropathy. The procedure begins with harvesting between 50 and 500 ml of bone marrow from the patient's posterior ilium and processed with a kit (a closed-bag system) that isolates CD19+ cells in a relatively pure formulation. Prior to delivery of these cells, the patient's renal arteries are cannulated with a delivery catheter designed specifically for delivery of solutions to the renal arteries. Delivery of the purified cells into the artery is achieved with injection of the cells into the catheter. An improvement in renal function is observed over the next several weeks after administration of the B cells.

Example 9

Treatment of a Human Patient Undergoing Kidney Transplantation

A patient suffering from end stage renal disease undergoes transplantation of a kidney from a tissue matched donor. Prior to implantation, between 50 and 500 ml of bone marrow is harvested from the patient's posterior ilium and processed with a kit (a closed-bag system) that isolates CD19+ cells in a relatively pure formulation. These isolated B cells are then injected throughout the donor kidney prior to surgically implanting the kidney. An improvement in renal function and organ rejection is observed over the next several weeks after administration of the B cells.

Example 10

Isolation of B Cells from Human Bone Marrow

In this example, bone marrow is chosen as the source of B cells and is selected by positive immunomagnetic separation. Human autologous bone marrow B cells are isolated in a specially designed separation chamber with collection bags attached that enable both fluid transfer and the separation process in a closed and sterile environment. All materials used in this B cell selection process are sterile. The collected bone marrow is loaded into the separation chamber where it is diluted 1:2 with phosphate buffered saline (PBS) and then layered onto a Ficoll density gradient contained within the centrifugation section of the chamber. The bone marrow cells are subjected to density gradient centrifugation. The upper Ficoll layer is directed towards a discard bag. The bone marrow mononuclear cells (MNCs) contained within the intermediate layer are detected by optical sensors, collected and washed with PBS. The washed MNCs are directed towards a collection bag containing antibody directed against the B cell specific antigen, CD19, and conjugated to a micromagnetic bead. The cells are incubated with the antibody-micromagnetic bead at a controlled temperature for 20 minutes. A magnet is then applied to the collection bag so that the cells attached to the antibody-micromagnetic bead are held against the side of the collection bag. The cells that did not bind to the antibody are removed. The magnet is then moved away from the bag and the cells bound to the antibody-micromagnetic beads are suspended in buffer containing a peptide recognized by the CD 19 that displaces the cells from the antibody. A magnet is again applied to the bag and the released CD19+ B cells are removed and collected. The B cells are washed onto a sterile filter that separates the cells from unbound peptide which flows through the filter into a discard tube. The B cells are resuspended in buffer and are ready for transplantation back into the patient.

Materials (All Materials are Sterile)

Some of the materials used in this example include a centrifugation chamber, stopcock manifold, connection units, connection lines, port for input product, ports for washing solutions, ports for resuspension, port for output product with needle injection site, needleless luers, collection bags or tube, waste bags, input line breakaway, vials for final product, 0.2 um filters, phosphate buffered saline (PBS), cell transplantation buffer, Ficoll solution, and CD19 antibody conjugated to micromagnetic beads.

Example 11

Isolation of B Cells from Human Blood

In this example, whole blood is chosen as the source of B cells and is selected by negative affinity separation. Human autologous peripheral blood B cells are isolated in a specially designed separation chamber with collection bags attached that enable both fluid transfer and the separation process in a closed and sterile environment. All materials used in this B cell selection process are sterile. The collected blood is loaded into the separation chamber where it is directed towards the centrifugation chamber. Following centrifugation of the blood cells, the upper layer containing plasma is directed towards a discard bag. The enriched leukocytes contained within the intermediate layer, the buffy coat, are detected by optical sensors and are directed towards a collection bag. The cells are washed with PBS and resuspended in buffer containing antibodies directed against non-B cell specific antigens conjugated to CNBr-activated Sepharose. The antibodies used are directed against the following human cell surface antigens: CD2, CD3, CD14, CD16, CD36, CD43, CD56, and glycophorin A that reside on T cells, NK cells granulocytes, monocytes/macrophages, and erythrocytes. The cell-antibody mixture is incubated at a controlled temperature for 20 minutes and then loaded into an empty column. Elution buffer is added to the column and the cells not bound to antibody, the B cells, are eluted. The B cells are washed with PBS, resuspended in buffer and are ready for transplantation back into the patient.

Materials (All Materials are Sterile)

Some of the materials used in this example include a centrifugation chamber, plastic column with stopcock, stopcock manifold, connection units, connection lines, port for input product, ports for washing solutions, ports for resuspension, port for output product with needle injection site, needleless luers, collection bags, waste bags, input line breakaway, vials for final product, phosphate buffered saline (PBS), cell elution buffer, cell transplantation buffer, cell lineage specific antibodies (anti-CD2, CD3, CD14, CD16, CD36, CD43, CD56, and glycophorin A) conjugated to CNBr-activated Sepharose.

All patents, publications and abstracts cited above are incorporated herein by reference in their entirety. It should be understood that the foregoing relates only to preferred embodiments of the present invention and that numerous modifications or alterations may be made therein without departing from the spirit and the scope of the present invention as defined in the following claims.

What is claimed is:

1. A method of treating injured ischemic tissue in an animal or a human comprising administering an amount of a composition comprising a relatively pure population of autologous isolated B cells in a pharmaceutically acceptable carrier to the animal or the human with the injured ischemic tissue, wherein the amount is effective to treat the injured ischemic tissue, wherein the relatively pure population of the isolated B cells is prepared by a method comprising substantially removing stem cells from a heterogeneous population of cells containing the stem cells and the B cells to create the relatively pure population of the isolated B cells.

2. The method of claim 1, further comprising administering a substance to the animal or the human that increases B cell concentration at the injured ischemic tissue in the animal or human.

3. The method of claim 1, further comprising administering a substance which facilitates restoration of function of the injured ischemic tissue, function of the relatively pure population of B cells or survival of the relatively pure population of B cells administered to the animal or the human.

4. The method of claim 1, wherein the B cells are derived from bone marrow, lymph nodes, spleen, or blood.

5. The method of claim 1, wherein the B cells are CD19+, B220+, or B cell receptor (Ig$\alpha\beta$)+ cells, or a combination thereof.

6. The method of claim 1, wherein the injured ischemic tissue is cardiac tissue.

7. A method for treating injured ischemic tissue in an animal or a human comprising:
   obtaining a sample containing B cells from the animal or the human with the injured ischemic tissue;
   purifying the sample to produce a relatively pure population of isolated B cells, wherein the relatively pure population of the isolated B cells is prepared by a method comprising substantially removing stem cells from the sample containing a heterogeneous population of cells containing the stem cells and the B cells to create the relatively pure population of the isolated B cells;
   combining the relatively pure population of the isolated B cells with a pharmaceutically acceptable carrier to produce a composition; and
   administering the composition to the animal or the human with the injured ischemic tissue in an amount effective to treat the injured ischemic tissue in the animal or the human.

8. The method of claim 7, further comprising administering a substance which facilitates restoration of function of the injured ischemic tissue, function of the relatively pure population of B cells, or survival of the relatively pure population of B cells administered to the animal or the human.

9. The method of claim 7, wherein the sample containing B cells is obtained from bone marrow, lymph nodes, spleen, or blood.

10. The method of claim 7, wherein the B cells are CD19+, B220+ or B cell receptor (Ig$\alpha\beta$)+ cells, or a combination thereof.

11. The method of claim 7, wherein the injured ischemic tissue is cardiac tissue.

* * * * *

UNITED STATES PATENT AND TRADEMARK OFFICE
CERTIFICATE OF CORRECTION

PATENT NO. : 7,695,712 B2 Page 1 of 1
APPLICATION NO. : 11/406508
DATED : April 13, 2010
INVENTOR(S) : Mark C. Poznansky et al.

It is certified that error appears in the above-identified patent and that said Letters Patent is hereby corrected as shown below:

On the title page, Item (75) in the Inventors:

Please change the spelling of "Nicholas" to --Nicolas--

Signed and Sealed this

Eighth Day of June, 2010

David J. Kappos
*Director of the United States Patent and Trademark Office*